United States Patent [19]

Stevens et al.

[11] Patent Number: 5,112,621
[45] Date of Patent: May 12, 1992

[54] SUSTAINED RELEASE PHARMACEUTICAL COMPOSITION OF DILTIAZEM

[75] Inventors: Howard Stevens, Grande-Bretagne, Scotland; Maryvonne Chariot, Maisons-Alfort, France; Françoise Arnold, Plainsboro, N.J.; Gareth Lewis, Dourdan, France

[73] Assignee: Synthelabo, Paris, France

[21] Appl. No.: 559,429

[22] Filed: Jul. 26, 1990

Related U.S. Application Data

[63] Continuation of Ser. No. 286.871, Dec. 20, 1988, abandoned.

Foreign Application Priority Data

Dec. 21, 1987 [FR] France .................. 87 17855

[51] Int. Cl.⁵ .......... A61K 9/16; A61K 9/58; A61K 9/62
[52] U.S. Cl. .................. 424/497; 424/458; 424/461; 424/462; 424/465; 424/480; 424/482; 424/495; 427/3
[58] Field of Search .......... 424/480, 465, 497

[56] References Cited

U.S. PATENT DOCUMENTS

| | | | |
|---|---|---|---|
| 4,533,674 | 8/1985 | Schmidt et al. | 514/474 |
| 4,775,536 | 10/1988 | Patel | 424/482 X |
| 4,780,318 | 10/1988 | Appelgren et al. | 424/482 X |
| 4,800,087 | 1/1989 | Mehta | 424/497 |

FOREIGN PATENT DOCUMENTS

WO84/2843 8/1984 PCT Int'l Appl.

OTHER PUBLICATIONS

Patent Abstracts of Japan, vol. 11, No. 184, Jun. 12, 1987, JP-A-62 5915.
Patent Abstracts of Japan, vol. 11, No. 47, Feb. 13, 1987, JP-A-61 212517.

*Primary Examiner*—Thurman K. Page
*Assistant Examiner*—James M. Spear
*Attorney, Agent, or Firm*—Fleit, Jacobson, Cohn, Price, Holman & Stern

[57] ABSTRACT

A sustained-release pharmaceutical composition which comprises microparticles comprising an active principle, said microparticles being coated with a coating mixture comprising ethyl cellulose and an acrylic resin which is a polymerizate of acrylic and methacrylic ester, having a molecular weight of at least 100,000 and comprising units of formula:

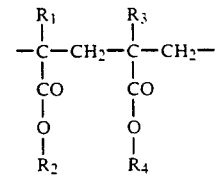

wherein:
 $R_1$ is hydrogen or methyl,
 $R_2$ is methyl or ethyl,
 $R_3$ is methyl; and
 $R_4$ is $-CH_2-CH_2N(CH_3)_3Cl$ the resin containing 5% of trimethylammonium methacrylate chloride units by weight.

9 Claims, No Drawings

SUSTAINED RELEASE PHARMACEUTICAL COMPOSITION OF DILTIAZEM

This application is a continuation of application Ser. No. 286,871, filed Dec. 20, 1988, now abandoned.

The present invention relates to a sustained-release pharmaceutical composition and to its preparation.

Sustained-release pharmaceutical dosage forms are very important in the pharmaceutical industry; they enable an active principle to be released gradually into the body and to be supplied with it over a long period. Furthermore, they spare the patient the trouble of repeatedly taking medicament.

Several sustained-release pharmaceutical dosage forms have already been proposed, for example tablets or hard gelatin capsules of coated microparticles.

The present invention provides a sustained-release pharmaceutical composition which comprises microparticles comprising an active principle, said microparticles being coated with a coating mixture comprising ethyl cellulose and an acrylic resin which is a polymerisate of acrylic and methacrylic ester, having a molecular weight of at least 100,000 and comprising units of formula:

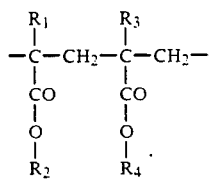

wherein:
$R_1$ is hydrogen or methyl;
$R_2$ is methyl or ethyl;
$R_3$ is methyl; and
$R_4$ is $-CH_2CH_2N(CH_3)_3Cl$
the resin containing 5% of trimethylammonium methacrylate chloride units by weight.

The present invention also provides a composition as defined above for use in a method of treatment of the human or animal body by therapy.

The composition of the present invention allows controlled dissolution of the active principle over a long period of time, independently of the pH.

The composition of the present invention may, for example, be in unit dosage form. In this case, the microparticles are generally contained in a hard gelatin capsule.

The acrylic resin can, for example, be that manufactured by Röhm Pharma GmbH under the trade mark "Eudragit RS". It is insoluble in water, natural and artificial gastrointestinal juices and buffered solutions, but swells and becomes permeable in these liquids.

The coating mixture preferably comprises the ethyl cellulose and the acrylic resin in a ratio of from 6:4 to 4:6, more preferably about 45:55, by weight.

The uncoated microparticles may also comprise excipients such as a diluent and a binder. The microparticles generally comprise the active principle in an amount of from 40 to 99%, especially about 80%, by weight based on the total weight of the uncoated microparticles.

The diluent may be, for example, microcrystalline cellulose. The binder may be, for example, polyvinylpyrrolidone, methylhydroxypropyl cellulose or, preferably, carboxymethyl cellulose.

The coating mixture may, for example, also comprise a plasticizer.

The plasticizer may, for example, be diethyl phthalate, dibutyl phthalate, an acetylated monoglyceride, propylene glycol, dibutyl sebacate, glycerol triacetate, a citric acid ester such as triethyl citrate, triethyl acetylcitrate, tributyl citrate, tributyl acetylcitrate or tri(2-ethylhexyl) acetylcitrate. An acetylated monoglyceride is preferably used.

Depending on the proportions of the two constituents of the coating mixture and the thickness of the coating film, the release rate of the active principle can be varied.

The coating mixture may be applied to the microparticles in a solvent, or suspending agent, or in a mixture of solvents, or suspending agents.

The solvent or suspending agent may, for example, be water or, preferably, an organic solvent or suspending agent such as acetone, ethyl acetate, methylene chloride or isopropyl alcohol. The mixture of solvents may, for example, be a mixture of isopropyl alcohol and acetone in relative proportions of from 10:90 to 90:10.

The coating mixture is generally present in the solvent or suspending agent or mixture of solvents or suspending agents, in a proportion of from 4 to 8%.

The composition of the present invention is prepared in two stages: the microparticles are first manufactured, and then they are coated.

Thus the present invention provides a process for preparing a composition as defined above which comprises coating the microparticles with the coating mixture.

The manufacture of the microparticles may be accomplished by different methods, for example:
traditional assembling,
rotary granulation,
compaction, or
extrusion/spheronization.
The latter method is preferred.

The coating may, for example, be applied by spraying using a coating apparatus such as a traditional turbine, a ventilated turbine, an air-fluidized bed ("top-spray" or "bottom-spray" spraying with or without a column) or a rotary granulator (tangential spraying).

The coating is preferably carried out in an air-fluidized bed, by "bottom-spray" spraying with a column.

An example of a suitable active principle is diltiazem, especially diltiazem hydrochloride.

The composition of the present invention preferably comprises from 70 to 80% of active principle, by weight relative to the total weight of coated microparticles. Under these conditions, hard gelatin capsules containing the coated microparticles may, for example, comprise from 90 to 400 mg of active principle.

An Example of a dosage form is as follows:

| Microparticles | |
|---|---|
| Diltiazem hydrochloride | 80% by weight |
| Microcrystalline cellulose | 19% by weight |
| Carboxymethyl cellulose | 1% by weight |
| Coating | |
| Ethylcellulose N 22 NF | 41% by weight |
| Eudragit RS | 50% by weight |
| Acetylated monoglyceride Myvacet 9-40 | 9% by weight | in the form of a 6% strength solution in a 65:35 acetone/isopropyl alcohol mixture, which is sprayed until the coating represents approximately 4% of the dry weight of the microparticles.

We have carried out comparative studies of dissolution of uncoated and variously coated microparticles. The results are as follows:
- the dissolution of uncoated microparticles (containing only the active principle, especially diltiazem) is pH-dependent,
- the dissolution of microparticles coated with ethyl cellulose is pH-dependent,
- the dissolution of microparticles coated with Eudragit RS is pH-dependent,
- the dissolution of microparticles coated with an ethyl cellulose/Eudragit RS mixture, in proportions of from 40:60 to 60:40, is pH-independent.

The fact that the dissolution of the sustained-release compositions of the invention is pH-independent is very important: the release of the active principle is independent of the medium throughout the length of the gastrointestinal tract, and can take place evenly.

We claim:

1. A sustained release pharmaceutical composition, comprising microparticles which contain diltiazem hydrochloride and which are coated with a coating mixture consisting essentially of ethyl cellulose and an acrylic resin in a ratio of from 6:4 to 4:6 by weight, wherein said resin is a polymerisate of acrylic and methacrylic esters, has a molecular weight of at least 100,000 and is comprised of 5% by weight trimethylammonium methacrylate chloride units and units that have the general chemical formula:

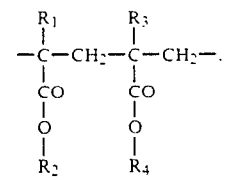

wherein:
$R_1$ is hydrogen or methyl;
$R_2$ is methyl or ethyl;
$R_3$ is methyl, and
$R_4$ is $-CH_2CH_2N(CH_3)_3Cl$.

2. A process for preparing a composition as defined in claim 1, which comprises coating the microparticles with the coating mixture.

3. A composition according to claim 1 wherein the coating mixture comprises the ethyl cellulose and the acrylic resin in a ratio of about 45:55 by weight.

4. A composition according to claim 1, wherein the coating mixture also comprises a plasticizer.

5. A composition according to claim 4, wherein the plasticizer is an acetylated monoglyceride.

6. A composition according to claim 1, wherein the microparticles also comprise a diluent and a binder.

7. A composition according to claim 6, wherein the diluent is microcrystalline cellulose.

8. A composition according to claim 6, wherein the binder is carboxymethyl cellulose.

9. A composition according to claim 1, which is in unit dosage form.

* * * * *